United States Patent [19]

Sagusa et al.

[11] 4,318,615
[45] Mar. 9, 1982

[54] AUTOMATIC RATE ANALYZING METHOD

[76] Inventors: Hisayuki Sagusa, 1280-4, Tabiko, Katsuta-shi; Hiroshi Hashimoto, 1616, Toyooka, Tokaimura, Naka-gun, Ibaraki-ken; Yasushi Nomura, 433-5, Yonesawacho, Mito-shi; Takehide Satou, 400-6; Ryohei Yabe, 6623, both of Ichige, Katsuta-shi, all of Japan

[21] Appl. No.: 27,849

[22] Filed: Apr. 6, 1979

[30] Foreign Application Priority Data

Apr. 10, 1978 [JP] Japan ............................ 53-41181

[51] Int. Cl.³ .......................... G01J 3/42; G01T 1/00
[52] U.S. Cl. .................................. 356/320; 250/328
[58] Field of Search ............... 356/306, 307, 317, 320, 356/321; 250/328

[56] References Cited

U.S. PATENT DOCUMENTS 3,701,601  10/1972  Plumpe, Jr. et al. ............. 356/320
4,063,817  12/1977  Shimamura et al. ............. 356/320

Primary Examiner—Alfred E. Smith
Assistant Examiner—Janice A. Howell

[57] ABSTRACT

An automatic rate analyzing method for determining a concentration of an item in concern contained in a sample to be analyzed comprises steps of irradiating the sample with light thereby to produce a transmitted light signal at a specific wavelength, converting the transmitted light signal into a corresponding electric signal and sampling the electric signal at a given interval thereby to produce a plurality of sample values. The plurality of sample values are grouped into groups each containing a predetermined number of sample values selected for every given number of the sample values. Each of the groups is deviated from the adjacent ones by a number of sample values smaller than the given number. The sample values in each of the groups are added together to produce sums associated with each of the groups. Difference between the sums of every two adjacent groups is determined and divided by the sum associated with either one of the two adjacent groups thereby to produce quotients which are then added together to produce a total sum representing the concentration of the item in concern.

9 Claims, 7 Drawing Figures

AUTOMATIC RATE ANALYZING METHOD

BACKGROUND OF THE INVENTION

The present invention relates in general to an automatic rate analyzing method and in particular concerns an improvement of an automatic rate analyzing system with a view to enhancing a sample processing speed.

Lately, reaction rate measuring methods (hereinafter referred to also as rate method in abridgment) have been increasingly adopted in field of the clinical biochemical analysis. The rate method is in principle advantageous over the hitherto known colorimetric analysis in that relatively high accuracy of measured values can be attained with the endogenous error being suppressed to a minimum. However, the rate method is inferior to the colorimetric analysis in respect of the time required for processing a sample because examination or observation of the individual sample to be analyzed takes a relatively long time. In spite of the fact that many and various attempts have been made in an effort to increase the processing speed of various automatic analyzing apparatus, there is still unavailable a system which can satisfy the desire and demand of users in respect of both the accuracy or precision of measurements and the speed at which the sample to be examined is processed.

As the means for increasing the processing speed of the rate analysis in the automatic analyzing apparatus the following measures are conceivable:

(1) Improving the stability and resolution of a photometer as used (e.g. by lowering the lower limit of analysis).
(2) Decreasing the dilution ratio (the ratio in quantity between a sampled serum and a final solution).
(3) Simultaneous measurement of plural samples in parallel.
(4) Development of high sensitive reaction series and reagents.

In conjunction with the first mentioned photometer, studies and developments have been made on the diffraction grating, high energy light source, semiconductor sensor and the like. At present, the stability on the order of $1 \times 10^{-4}$ OD (optical density, absorbance) has been attained.

When the dilution is decreased, i.e. part of serum is increased, the sensitivity of the substance to be analyzed (variation in absorbance) is correspondingly increased, thereby to allow the rate measurement to be carried out in a short time. However, the accuracy which is one of the most advantageous features of the rate analysis undergoes degradation, whereby the range of measurement is disadvantageously restricted. For this reason, the reduction of the dilution is unfavorable. Practically, the ratio of dilution is preferably in the range of 30 to 60 in the conventional automatic analyzer apparatus. Lately, an automatic analyzing apparatus of a discrete type has been commercially available which is capable of accomplishing the reaction rate measurement of a single sample for about twenty seconds by using the dilution ratio on the order of 10, thereby to permit the processing to be carried out at a speed of 120 samples/hour. However, there is a problem remaining to be solved in respect of the attainable accuracy.

As to the parallel measurements of plural samples, there is typically known as apparatus called the Anderson's centrifugal system. With this apparatus, it is certainly possible to process several tens of samples for several minutes so far as the photometry is concerned. However, due to the rotary system as adopted, there arise difficulties in respect of linkage to other analyzing operations such as pippetting, dispensing, incubation, washing or the like. Additionally, it is impossible to carry out measurements simultaneously on plural items. After all, the processing speed can not be increased as a whole to a desired degree.

Development of new reaction series and reagents is certainly one of the most important problems to be solved, which however requires intrinsically a train of repeated try-and-error processes and is not adapted to a straightforward solution.

Notwithstanding the circumstances described above, there is at present a pressing demand for the automatic rate analyzer apparatus of the discrete type which can be operated in a facilitated manner at an increased processing speed with an enhanced accuracy and precision. One advantageous feature of the discrete type automatic rate analyzing apparatus resides in that a number of items can be simultaneously and continuously measured in a set of reaction series. On the other hand, this type of analyzing apparatus has a drawback in that the operation speed of the whole system has to follow the processing speed at the photometrical station because the individual chemical controls and manipulations including measurements are carried out on a continuous line base. A typical example of such automatic rate analyzing apparatus is disclosed in U.S. patent application Ser. No. 834,902 filed Sept. 20, 1977 by K. Yamashita, H. Umetsu, K. Heguri and K. Yoshida under the title "Automatic Chemical Analyzing Method and Apparatus" and assigned to the assignee of the present application, which application corresponds to Japanese patent application No. 51-114226(1976) filed Sept. 22, 1976 by the present assignee under the title "Automatic Chemical Analyzing Apparatus" and disclosed publicly Apr. 10, 1978 as Japanese Laid-Open patent application No. 53-39192(1978).

In the case of the automatic rate analyzing apparatus disclosed in the patent applications cited above, a number of samples or specimens (sera) each added with reagent are discretely transported on a reaction line. The samples in which chemical reactions have been brought about are individually irradiated by light radiation during the transportation, whereby the quantity of light of a specified wavelength transmitted through the individual sample is measured by a spectrophotometer twice at different time points. Then, the absorbances at the different time points are arithmetically determined on the basis of the measured values through logarithmic calculation. From the difference in the calculated absorbances, variation in the absorbance of the individual sample during the predetermined time is arithmetically determined and used to represent the concentration or activity of the concerned items in the serum. In the rate analyzing apparatus described above in which the magnitude of variation in the absorbance is determined in terms of the difference in absorbance at two different time points, i.e. at the beginning and the end of the photometery period, there arises a problem that the stability of the photometer system becomes degraded due to possible noise, particularly when the number of samples is small. Further, in order to detect the activity of the item in concern with a reasonable accuracy, the period during which the sample to be analyzed is examined by the photometer system has to be correspondingly elongated, as the result of which the processing speed is necessarily decreased. In this respect, the automatic rate analyzing apparatus is inferior to the colorimetric analysis. Besides, the logarithmic calculation for determining the absorbance on the basis of the quantity of light transmitted through the sample will take a lot of time when the calculation is executed by using a microcomputer, providing an obstacle in increasing the processing speed. In this manner, the automatic rate analyzing apparatus described above has many problems remaining to be solved for satisfying the requirements imposed by the users in respect of the accuracy and precision as well as the sample processing speed.

The stability of the conventional photometer is on the order of $10^{-4}$ OD as described hereinbefore. On the other hand, in the popular rate measurement of enzymes GOT (glutamate oxalate transaminase) and GPT (glutamate pyruvate transaminase) in which the absorbance change of the reagent NADH is measured, the change or variation in absorbance for one international unit (1 mU/ml) is on the order of $1 \times 10^{-4}$ OD/mm at the dilution factor of 50. Accordingly, the time duration required for the photometry of one sample will amount to about 30 minutes in order to attain the rate measurement with a high accuracy, which in turn means that the processing speed of the analyzing apparatus as a whole is on the order of 60 samples/hour. Such processing speed is of course remarkably lower as compared with the processing speed in the conventional colorimetric analysis. There is certainly available a discrete type analyzing apparatus which is capable of processing 120 samples an hour by using a decreased dilution ratio. Such apparatus however is disadvantageous in respect of accuracy and allowable range of measurement, as described hereinbefore.

It should be mentioned that, in the automatic analyzing apparatus of the discrete type, the chemical controls or manipulations other than the photometry such as pippetting, dispensing, agitation, washing or the like can be carried out at a speed of about 10 seconds for a sample. Accordingly, when the processing speed at the photometric system is increased, a high speed automatic rate analyzing apparatus can be realized which permits a single sample to be processed within 10 seconds, i.e. an increased processing speed of about 360 samples for an hour.

In the case where one cycle is to be completed within 10 seconds, the time duration required for the rate photometry has to be in the range of 5 to 8 seconds, with the result that a variation or change in absorbance for the measurement of GOT and GPT becomes remarkably small on the order of $1.2 \times 10^{-5}$ OD to $8 \times 10^{-6}$ OD. The stability of the photometric system should then be about $1 \times 10^{-5}$ OD.

It should be additionally mentioned that, in the measurement of such minute change in absorbance as described above, the resolution of an A-D (analog-to-digital) converter used in the arithmetic operation brings about a problem in addition to the problem of stability. The problem of the resolution of A-D converter is serious in consideration of the fact that most of the rate reactions take place in a high range of absolute value of absorbance (e.g. 10 to 2.0 OD). The resolution of the commercially available A-D converter is at most on the order of 16 bits (in the binary system). Accordingly, the output of the A-D converter is about 2000 in decimal notation which means that the resolution power of the A-D converter represented in terms of absorbance is remarkably low as on the order of $2 \times 10^{-4}$ OD.

For the determination of the absorbance change with a view to enhancing the stability of the photometric system inclusive of the succeeding data processing parts, the absorbance is measured $2m+1$ times and a regression line is determined through the least square approximation. Then, the absorbance change $\Delta ABS$ over the whole photometry period is determined on the basis of the slope of the regression line. Namely, $$\Delta ABS = 2m \cdot \sum_{x=-m}^{m} Ax \cdot X / \sum_{x=-m}^{m} X^2 \qquad (1)$$

where x represents time points obtained by dividing the measuring period by $2m+1$, and Ax thus represents the absorbance at the time point x. The stability of the photometric system inclusive of the data processing parts can be enhanced through the procedures described above. In this connection, an increased number of data samplings brings about a correspondingly improved stability. In general, assuming that noise components are present in the Gaussian distribution, the stability, of the whole photometric system becomes substantially $1/\sqrt{m}$ after the procedure described above. However, when the above arithmetic procedure is to be executed by a computer, then there arises a problem in connection with the processing speed of the employed computer. This problem is serious particularly when the arithmetic processing is to be executed by a micro-computer adopted usually in the automatic rate analyzing apparatus. In the determination of the absorbance change on the basis of the mathematic expression (1), the time consuming process is the logarithmic computation for determining the absorbance A from the transmissivity T. For example, if the calculation based on the equation (1) is to be executed by the conventional micro-computer, then 70 to 80% of the whole calculation time will be consumed for the logarithmic operation.

As will be appreciated from the foregoing discussion, there has not been known yet a rate analyzing method which can assure high accuracy and precision of measurement at a high processing speed.

SUMMARY OF THE INVENTION

Accordingly, an object of the invention is to provide an automatic rate analyzing method which evades the drawbacks of the hitherto known method such as described above.

Another object of the present invention is to provide an improved rate analyzing method which allows rate analyses to be performed with high accuracy and precision at a high sample processing speed.

In view of the above and other objects which will become apparent as description proceeds, there is proposed according to a general aspect of the invention an automatic rate analyzing method which comprises steps of dividing sample a values obtained by sampling transmissivity signal for a plurality of sampling times into groups each including a predetermined number of sample values selected for a predetermined number of the sampling times, each of the groups being different from the adjacent groups by a number of samples smaller than the predetermined number of the sample values, adding together the sample values in each of the groups thereby to produce sum values, determining the difference in the sum values for every two adjacent groups and dividing the obtained difference value by the sum value of one of the two adjacent groups thereby to produce a quotient, adding together the quotient values obtained for every two adjacent groups thereby to produce a total sum, and arithmetically determining the concentration of a concerned item contained in the sample to be analyzed on the basis of the total sum.

The above and other objects, features and advantages of the invention will be readily understood by examining the following description taken, by way of example only, in conjunction with the accompanying drawings.

DESCRIPTION OF THE PREFERRED EMBODIMENTS

Figure 1:
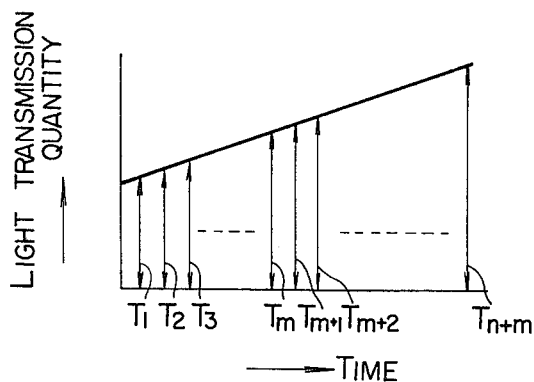
FIG. 1 is a diagram to illustrate the principle of the invention.

In the first place the principle of the automatic rate analyzing method according to the invention will be described.

The term which is inherently required for the rate analysis measurement is not the absolute values Ax of absorbance at the individual measuring time points but change or variation $\Delta ABS$ in absorbance during a preselected measuring period. In this connection, it is noted that the value of absorbance change $\Delta ABS$ becomes remarkably small when the measuring period for a single sample is selected to be shorter with a view to increasing the processing speed at the photometric system. By the way, in accordance with the definition of the term absorbance, a minute change $\Delta T$ in the transmissivity or transmission quantity is in a relationship to a minute or fine change $\Delta A$ in absorbance which can be mathematically expressed as follows:

$$\Delta A = -(\log_{10} e) \cdot \ln\left(1 + \frac{\Delta T}{T}\right) \quad (2)$$

where T represents a transmission quantity at the time point at which the photometric measurement is started.

From the Maclaurin's theorem, the expression (2) can be developed as follows:

$$\Delta A = -(\log_{10} e) \left\{ \frac{\Delta T}{T} - \frac{1}{2}\left(\frac{\Delta T}{T}\right)^2 + \frac{1}{3}\left(\frac{\Delta T}{T}\right)^3 - \frac{1}{4}\left(\frac{\Delta T}{T}\right)^4 \cdots \right\} \quad (3)$$

when $\Delta T/T \ll 1$, the following expressions applies valid.

$$\Delta A = -(\log_{10} e)(\Delta T/T) = -0.4343(\Delta T/T) \quad (4)$$

In other words, when the preselected photometric measuring period is divided into minute intervals for sampling corresponding transmissivities and the absorbance change $\Delta A$ is determined for every divided interval in accordance with the formula (4), it is then possible to determine the change in absorbance $\Delta ABS$ within the preselected period from the total sum of the absorbance changes $\Delta A$ in the divided intervals, as can be mathematically expressed as follows:

$$\Delta ABS = -0.4343 \sum_{x=1}^{n} \frac{T_{x+1} - T_x}{T_x} \quad (5)$$

where $T_x$ represents the sampled value of the transmission data at the x-th time interval or time point, and $T_x$ represents the sampled transmission quantity or value at the time point $x+1$.

It will be thus appreciated that logarithmic calculation is no longer required for the data processing which can be accomplished arithmetically by simple subtraction and division in a short time. Further, the number n of times for sampling the transmissivity or transmission quantity can be advantageously increased. It goes without saying that the increased data sampling number n will result in a correspondingly enhanced stability of the photometric system against noise components. For example, when a micro-computer of 16 bits which is one of the most popular computers is used for arithmetically determining the absorbance change $\Delta ABS$ in accordance with the equation (5), calculation for the single $\Delta ABS$ can be realized within 10 m sec, whereby the data sampling at the rate of 100 times/sec can be attained. It should be noted that, although the stability is improved by increasing the sampling number or frequency n, the resolution remains unchanged, because the overall resolution at which the absorbance change $\Delta ABS$ is arithmetically determined on the basis of the digitally converted transmission data is determined in dependence on only the bit capacity of the A-D converter independently from the sampling frequency n.

Accordingly, with a view to enhancing the resolution, the invention teaches that a plurality of digitally converted transmission data are combined into a single transmission data which is then arithmetically processed. More particularly, the automatic rate analyzing method according to the invention comprises the following steps of:

obtaining a number of sample values by sampling transmission quantity data at a given time interval, dividing the number of the sample values into groups each containing a predetermined number of the sample values selected for every predetermined number of sampling, wherein each of the groups is deviated from the adjacent groups by a given number of sample values which is smaller than the aforementioned predetermined number, adding together the sample values in each of the groups thereby to produce sum values, determining arithmetically differences in sum values each between the adjacent two groups and dividing the difference by the sum value of either one of the two adjacent groups thereby to produce quotient values, and adding together the quotient values thereby to produce a total sum value which is utilized to represent the absorbance change $\Delta ABS$.

Now, referring to FIG. 1, description will be made on an exemplary rate analyzing method in which a number of sample values are divided into groups each containing a predetermined number of successive sample values, each group being deviated or separated from the adjacent groups by one sample, whereby the arithmetic operation described above is executed on the basis of these groups.

In the first place, n transmission quantity data (sample values) $T_x$ are classified into groups each containing m transmission data values and being offset from the adjacent groups by a single data value. More specifically, a first group contains the sample values or sampled transmission quantity data $T_1$ to $T_m$, a second group contains the sampled transmission data $T_2$ to $T_{m+1}$, a third group contains the sampled transmission data $T_3$ to $T_{m+2}$, and so forth. In this manner, n transmission data values are classified into (n-m) groups each containing m sampled data. In each of the groups, all of the transmission data values are added together thereby to obtain the summed transmission quantity data $T'_x$ which is then processed arithmetically in accordance with the formula (4). In other words, n transmission quantity data are transformed into (n-m) transmission quantity data $T'_x$ each consisting of a combination of m sample transmission data.

The summed transmission quantity data $T'_x$ in each of the groups can be expressed as follows:

$$T'_1 = \sum_{x=1}^{m} T_x$$

$$T'_2 = \sum_{x=2}^{1+m} T_x$$

$$\vdots$$

$$T'_{n-m} = \sum_{x=n-m}^{n} T_x$$

Accordingly, the change in absorbance $\Delta ABS$ is given by:

$$\Delta ABS = -0.4343 \sum_{x=1}^{n-m} \frac{T'_{x+1} - T'_x}{T'_x} \quad (6)$$

It has been found that the resolution is improved by a factor of about 1/m in accordance with the formula (6) as compared with the equation (5). The results are listed in the following Table 1.

TABLE 1

| m | Overall Resolution |
|---|---|
| 1 | $1.2 \times 10^{-4}$ |
| 5 | $2.4 \times 10^{-5}$ |
| 10 | $1.3 \times 10^{-5}$ |

TABLE 1-continued

| m | Overall Resolution |
|---|---|
| 20 | $9.2 \times 10^{-6}$ |

For example, when m is selected to be equal to a number in the range of 10 to 20, an adequate resolution on the order of $1 \times 10^{-5}$ can be obtained.

Figure 2:
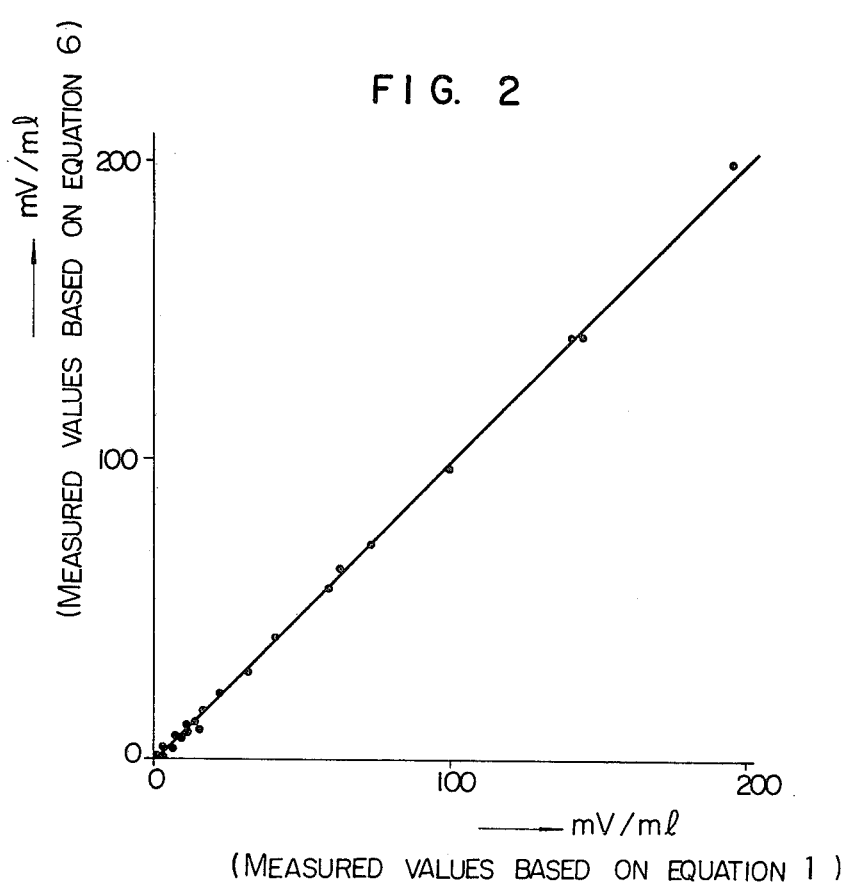
FIG. 2 is a graph to illustrate measured values obtained in accordance with a rate analyzing method according to the present invention in comparison with those obtained through a hitherto known process.

FIG. 2 illustrates graphically the correlation between the absorbance changes $\Delta ABS$ determined in accordance with the equations (1) and (6), respectively, in the case in which the rate measurements of GOT in various sera were conducted at a dilution ratio of 40. The photometric period is equal to 8 seconds, while the number n of samplings is equal to 820 and m is selected equal to 20. As can be seen from FIG. 2, the correlated values are distributed along a straight line having a slope of about 45° over a range from a low international unit to a high unit, which means that the approximated calculations on the basis of the expressions (5) and (6) can be practically and validly employed. The following Table 2 shows reproducibility in the calculation according to the equation (6) in comparison with the equation (1) for the repeated rate measurements using the same control serum.

TABLE 2

| Calculation based on Equation (6) | Calculation based on Equation (1) |
|---|---|
| 82 | 82 |
| 82 | 82 |
| 81 | 80 |
| 82 | 82 |
| 81 | 82 |
| 80 | 82 |
| 82 | 81 |
| 82 | 79 |
| 82 | 82 |
| 80 | 82 |
| 82 | 82 |
| 82 | 82 |
| 82 | 82 |
| 82 | 81 |
| . | . |
| . | . |
| . | . |
| . | . |
| . | . |
| . | . |
| . | . |

As can be seen from the contents of the Table 2, the reproducibility in the case in which equation (6) is used for calculation is quite comparable to the results attained by using the equation (1). It is to be noted that use of the equation (6) reduces the time required for the calculation to 1/5 to 1/10 of the time required for the calculation on the basis of the equation (1), since the former involves no logarithmic calculation, whereby the data sampling frequency n can be adequately increased even in the automatic rate analyzing apparatus the data processing speed of which is relatively low. In this manner, according to the principle of the invention, it is possible to improve the total stability and resolution and thus provide an automatic rate analyzing apparatus having a significantly improved sample processing capability which makes it possible to effect the rate measurement every time within 10 seconds by using a high dilution ratio.

Next, description will be made on an exemplary embodiment of the automatic rate analyzing apparatus which is adapted to execute the data processing according to the principle of the invention.

Figure 3:
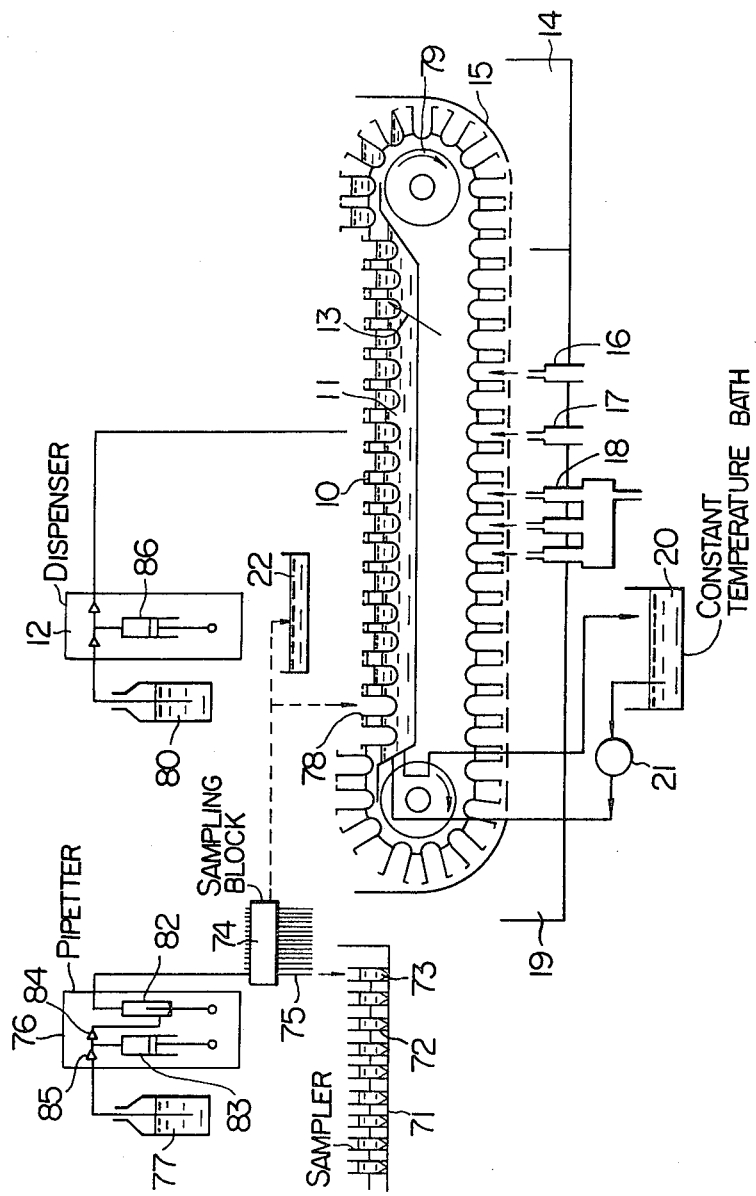
FIG. 3 shows schematically a general arrangement of an automatic rate analyzing apparatus to which the principle of the invention can be applied.
Figure 4:
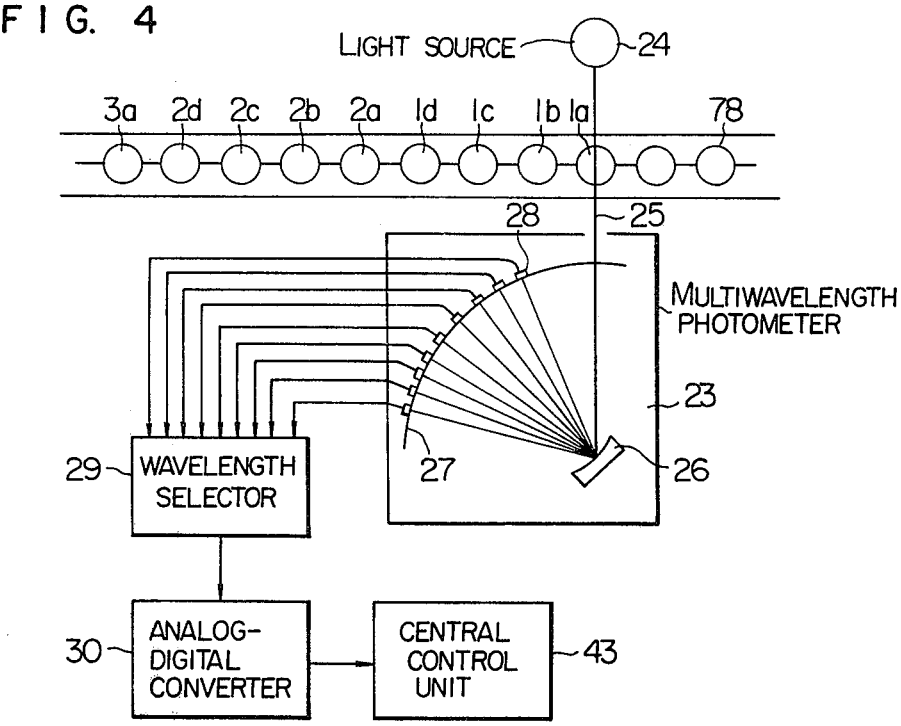
FIG. 4 schematically illustrates an optical system of the automatic rate analyzing apparatus to which the invention can be applied together with a data processing system adapted to be used for carrying out a rate analyzing method according to the invention.

FIGS. 3 and 4 show a general arrangement of a typical automatic rate analyzing apparatus of a discrete type adapted to carry out the method according to the invention. The analyzing apparatus comprises in general a sampler for supplying samples to be analyzed, a metering system for metering the sample and reagent, a reaction system for promoting reaction of the sample with the reagent, a photometric sensor unit for measuring the samples having undergone the reaction, a data processing unit and a central control unit for supervising and controlling operations of the whole apparatus.

Referring to FIG. 3, the sampler 71 is adapted to transport successively a series of many sample tubes 72 coupled flexibly to one another to a predetermined sampling position. A sample or specimen is contained in each of the sample tubes 72. The samples 73 having the same item to be analyzed are grouped in one set. The samples belonging to the same group are contained in a train of the sample tubes 72. The tube trains for different kinds of samples are connected in cascade. There is disposed at the boundary between the individual groups a marker tube or container which has a unique configuration such as the one provided with an annular projection. Thus, the boundary between the sample groups can be identified by the marker tube.

The sampling block 74 comprises twelve nozzles 75 which are adapted to be independently moved downwardly in response to the command from the central control unit 43. Each nozzle is connected to the pippetter 76. Although not shown, twelve pipetters 76 are provided. Each pipetter 76 comprises a micro-cylinder 82 and a metering pump 83. The micro-cylinder and the plunger of pump are adapted to be driven by an air cylinder or cam drive mechanism which is controlled in response to the command from the central control unit. Reference numerals 84 and 85 denote check valves. The sampling block 74 is adapted to be horizontally moved to a predetermined position by a pulse motor operated under the command from the central control unit. When the sample 73 within the sample tube 72 located at the sampling position is to be sucked up by the nozzle 75, the sampling block 74 is so moved that the associated one of the twelve nozzles comes to the position immediately over the sampling position, and then the associated nozzle is moved downwardly into the sample tube 72. Subsequently, the plunger of the micro-cylinder 82 is driven thereby to suck up a predetermined quantity of the sample 73. Simultaneously, the metering pump 83 is driven to suck up a predetermined quantity of regent from the container thereof. After the nozzle 75 inserted into the sample tube has been moved upwardly to the original position, the sampling block 74 is caused to be moved to the right as viewed in the drawing to a predetermined position at which the nozzle is inserted into a reaction vessel 78 to discharge the sample therein together with reagent. Thereafter, the nozzle 75 is washed in a cleaning bath.

Referring to FIG. 4 which illustrates the photometric sensor and the data processing system of an automatic rate analyzing apparatus for carrying out the method according to the invention, it is assumed that a solution a identified by the sample number 1 is to be measured in respect of four items. Although the solution is measured at slightly different times for each item, it is assumed that the measurement is performed simultaneously for the four items. The train of transparent reaction vessels are moved intermittently through a constant temperature bath 11, whereby the solution 1a which has undergone the reaction is temporarily stopped at a position where the light flux 25 emitted from a light source such as a tungsten lamp 24 passes through the solution 1a to be absorbed by it. The light flux or beam 25 impinges on a concaved diffraction grating 26 of a multi-wavelength photometer 23, as the result of which dispersed spectra will be focused on a Rowland's circle 27 along which sensor or detectors 28 in number corresponding to that of the wavelengths to be measured are disposed. The output signals from the detectors 28 are applied to a wavelength selector circuit 29 which includes a switch circuit controlled under the command from the central control unit 43, whereby the output signal from the sensor 28 detecting the wavelength corresponding to the item a to be analyzed is selected and applied to an analog-to-digital or A-D converter 30. The output from the A-D converter 30 is supplied to the central control or processing unit 43 so as to be arithmetically processed.

In response to the next timing signal, the reaction vessel 78 containing the solution 1b which has undergone reaction is moved to the position to be irradiated by light flux, and the photometry is carried out in the manner described above. However, the wavelength is selected by the wavelength selector circuit 29 in dependence on the item b to be analyzed. Similar processing is performed on the solutions 1c and 1d. Succeeding solutions 2a, 2b, 2c and 2d identified by the solution number 2 and having items a, b, c and d to be analyzed are processed in the similar manner as the solutions labelled with the solution number 1. Similar processing is made on the further solutions.

The central control or processing unit 43 includes a micro-computer 33 as a primary component and connected to the various function units through a bus line 34. A program for operating the sampler 1, the sampling block 74, the pippetter 76, sprockets 79, the dispenser 12 and so forth shown in FIG. 3 is stored in a read-only memory 35. A random access memory 36 is used for the arithmetic operation and storing variable data. The measurement data selected by the wavelength selector circuit 29 is supplied to the unit 43 through the A-D converter 30 and subjected to an arithmetic processing operation in the micro-computer 33 in dependence on the item to be analyzed. The results of the arithmetic operation are stored in the memory 36 and thereafter read therefrom in accordance with a previously programmed sequence to be displayed in a display unit 32 through a display interface 37.

The conditions for measurement such as the items to be analyzed of the individual sample groups, the operation timing of the various function units of the automatic chemical analyzing apparatus or the like are stored in the random access memory 36 through a panel interface 41 by operating a keyboard provided at a panel 42. During the analyzing operation, the measuring conditions stored in the memory 36 are supervised by the program stored in the read-only memory 35, whereby instructions are issued to drive the associated function units when the operating state of the automatic chemical analyzing apparatus coincides with the operating conditions of the function units. In this manner, the operation timing for the various function units of the automatic analyzing apparatus is controlled by the command supplied to the driver circuit 40 through a mechanism control interface 39.

Figure 6:
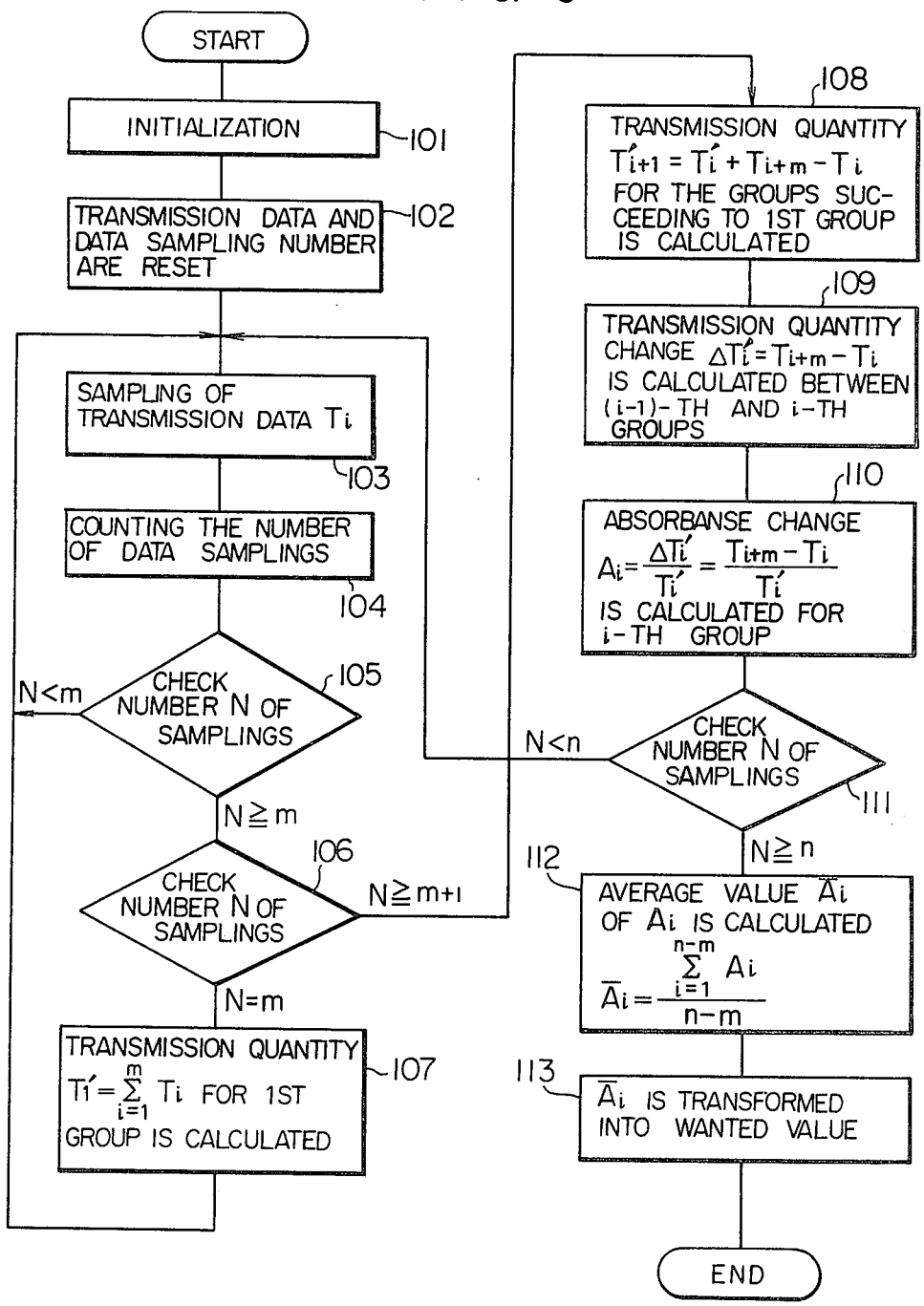
FIG. 6 shows a flow-chart illustrating processings executed by the data processing system shown in FIG. 5.

Next, description will be made on the data processing performed on the basis of the rate analyzing method according to the invention by referring to a flow chart shown in FIG. 6. By way of example, it is assumed that the change in absorbance of a single sample during a photometry period is measured to arithmetically determine the activity of the sample. The steps described below are executed in accordance with a program stored in the random access memory 36. At the step 101, initialization is made in precedence to the starting of operation of the automatic analyzing apparatus. In other words, the wavelength corresponding to the item of sample to be analyzed, the sampling period, the sampling frequency m (m=16 in the case of the illustrated example) at which transmission data of the samples belonging to one group are sampled, the sampling frequency n (n=100) at which all the transmission data required for calculating $\Delta ABS$ are sampled and the like are set at the random access memory or RAM 36. After the operation of the analyzing apparatus has been started, the wavelength selector circuit 29 supplies the output signal from the detector 28 corresponding to the preset wavelength to the A-D converter 30, the output from which is sampled over the preset period.

At the step 102, the transmission data and the number N of the sampled data stored in the RAM 36 are reset.

At the step 103, the transmission data $T_x$ of the preset wavelength subjected to A-D conversion is sampled from the output of the A-D converter 30 during the preset sampling period, and the sampled data is stored in RAM 35.

At the step 104, the number N of the sampled data is successively counted by a counter incorporated in the micro-computer 33 or RAM 36 as the sampling is performed.

At the step 105, check is made if the number N of the samplings exceeds the preset number m or 16. If N>16, then the program proceeds to the next step 106. Otherwise, the routine is returned back to the step 103.

At the step 106, the number of samplings is again checked. If N>17, the program proceeds to the step 108. If N=16, it proceeds to the step 107.

At the step 107, the first sampled value $T_1$ to the 16-th sampled value $T_{16}$, i.e. the sample values belonging to a first group are read out from the RAM and the transmission data T' of the first group are arithmetically determined on the basis of the sample values. More particularly, representing the transmission data sampled at the time point $t_i$ by $T_i$, a sum of the data sampled at the time point, $t_1, t_2, \ldots, t_{16}$ is determined, i.e.

$$T'_1 = \sum_{x=1}^{m} T_x = \sum_{x=1}^{16} T_x$$

is realized and the result is stored in the RAM 36. After this step, return is made to the step 103.

At the step 108, the transmission data $T'_{i+1}$ of the (i+1)-th group succeeding to the first group is arithmetically determined. Here, $i \geq 1$. The transmission data of the (i+1)-th group is represented by $$\sum_{x=i}^{i+m} T_{x+1}$$

which is determined by adding the final transmission data $T_{i+m}$ of the (i+1)-th group to the transmission data $T'_i$ $(T'_i = T_{i+1} + T_{i+m-1} - T_{i-1})$ of the i-th group stored in RAM and subtracting the first transmission data $T_i$ of the i-th group. In other words, a sum of the data sampled at the time points $t_{i+1}, t_{i+2}, \ldots, t_{i+m+1}$ is determined such that $T'_{i+1} = T'_i + T_{i+m} - T_i$ and the result is stored in RAM 36.

At the step 109, a change in the transmission quantity between the (i−1)-th group and i-th group, i.e. the change or variation $\Delta T'_i$ in the transmission data sampled between the time points $t_i$ and $t_{i+m}$ is arithmetically determined. In other words, $\Delta T'_i = T'_{i+1} - T'_i = T_{i+m} - T_i$ is calculated and the result is stored in RAM 36.

At the step 110, the change in absorbance $A_i$ at the individual sampling intervals in the i-th group, i.e. the absorbance change in the sampling period between the time point $t_i$ and $t_{i+m}$ is determined in accordance with $$A_i = \frac{\Delta T'_i}{T'_i} = \frac{T'_{i+1} - T'_i}{T'_i} = \frac{T_{i+m} - T_i}{T'_i}$$

by utilizing $T'_{i+1}$ and $\Delta T'_i$ obtained at the steps 108 and 109. The result is stored in RAM 36.

At the step 111, the number N of samplings counted by the counter is checked. If N<n (where n=100 in this example), the routine returns to the step 103. If N≧n, the transmission data sampling process is terminated and the program proceeds to the next step 112. In this manner, so long as N>m+1, the arithmetic operations at the steps 108 to 110 are repeated as each transmission data is sampled.

At step 112, an average value $\overline{A}_i$ of the absorbance changes $A_i$ in the first to the (n-m) groups is arithmetically determined. In other words, the average value of the absorbance changes between the time points $t_l$ and $t_n$ is determined by using the data $A_i$ stored in RAM in accordance with $$\overline{A}_i = \frac{\sum_{i=1}^{n-m} A_i}{n - m}.$$

At the step 113, the wanted value of the item in the sample is determined on the basis of the average value $\overline{A}_i$. When the sample contains serum, the concentration or activity of the enzyme in concern is determined. The result may be displayed on the display unit 38 through the display interface 37.

In the example described above, each of the transmission data groups includes n successive sampled data and is deviated from the adjacent groups by one sampled data. However, it will be appreciated that each group may contain n sampled data selected alternately from the successive data and be deviated from the adjacent groups by two sample data, thereby to arithmetically determine the absorbence change. In this case, the sums of the transmission data in the individual groups can be represented as follows:

$$T'_1 = \sum_{x=1}^{m} T_{2x-1}$$

$$T'_2 = \sum_{x=2}^{m+1} T_{2x-1}$$

$$T'_3 = \sum_{x=2}^{m+2} T_{2x-1}$$

$$\vdots$$

$$T'_i = \sum_{x=i}^{m+i-1} T_{2x-1}$$

The results of the above arithmetic operations are then used to determine the average value $\bar{A}_i$ of the absorbance changes.

Figure 5:
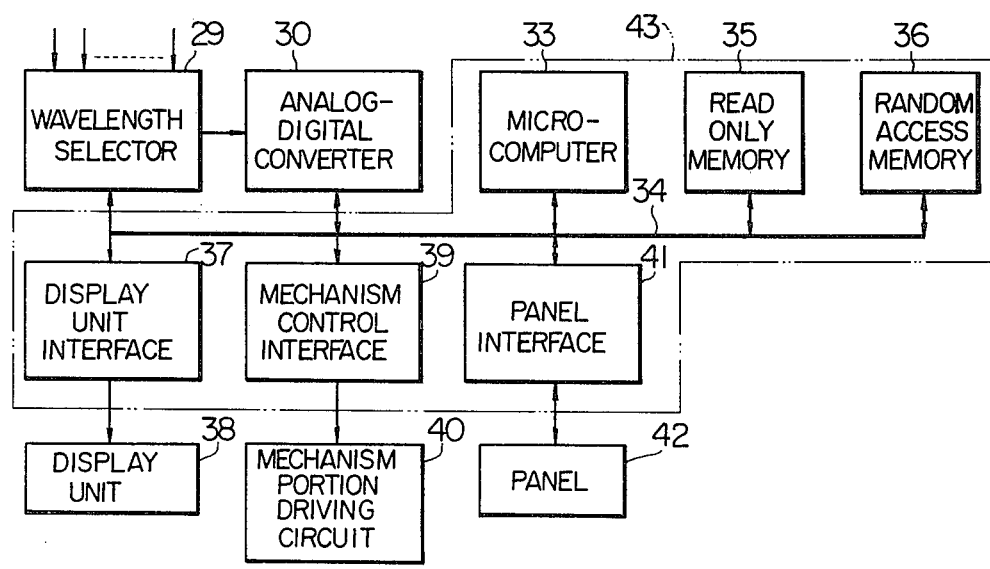
FIG. 5 is a block diagram showing a data processing system according to an exemplary embodiment of the present invention.
Figure 7:
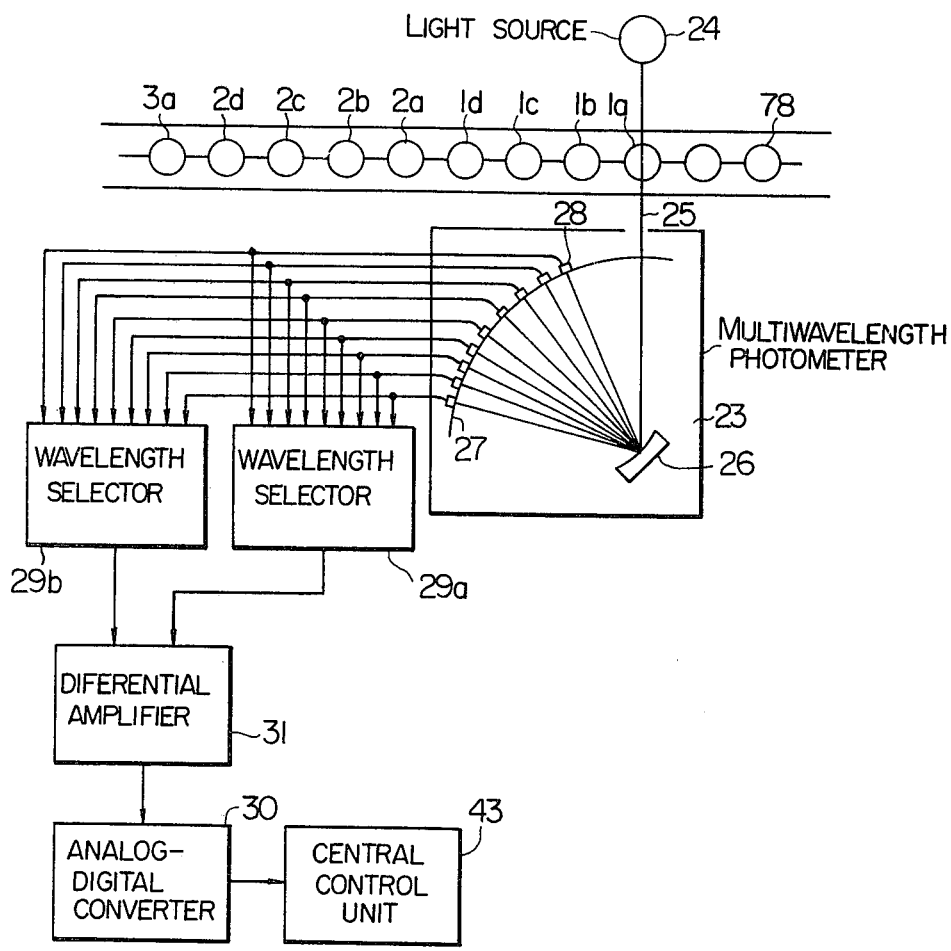
FIG. 7 shows schematically another exemplary embodiment of the data processing arrangement adapted to carry out the rate analyzing method according to the invention.

FIG. 7 shows another arrangement of the apparatus for carrying out the rate analyzing method according to another embodiment of the invention. Two detectors or sensors 28 producing output signals representative of the specific wavelength associated with the concerned item of the sample to be analyzed and the wavelength irrelevant to the item, respectively, are selected by wavelength selector circuits 29a and 29b. Difference between the transmission or transmissivity signals output from the wavelength selector circuits 29a and 29b and representing the two wavelengths is produced from a differential amplifier 31. The value of difference is then converted into a corresponding digital quantity by an A-D converter 30, which digital quantity is supplied to a central processing unit 43 at which the concentration or the like of the concerned item is arithmetically determined in the same manner as described hereinbefore in conjunction with FIGS. 5 et seq.

According to the method described just above in which the difference value in the transmission or transmissivity at the specific wavelength associated with the concerned item is determined with reference to the transmissivity at the wavelength irrelevant to the item, the change or variation in the light transmission quantity at the specific wavelength can be detected with a high accuracy, even when the base line of the transmission quantity undergoes variation or drifting due to noises such as variation in the intensity of a light source, contamination of the sample and so forth, since such drift of the base line can be cancelled by using the difference signal.

From the foregoing description, it will be appreciated that the invention has now provided a reaction rate analyzing method which allows the sample to be analyzed at an improved overall stability and resolution at a high processing speed.

We claim:

1. A method of automatically and optically analyzing a solution comprising:
    a first step of irradiating the solution to be analyzed with light thereby to produce a transmitted light quantity at a specific wavelength;
    a second step of converting said transmitted light quantity into an electrical transmission signal;
    a third step of producing a plurality of serial sample values by sampling said transmission signal at given intervals;
    a fourth step of grouping said plurality of the serial sample values into groups each containing a predetermined number of said sample values selected in accordance with the positional number of said sample values, each of said groups including samples whose positional number deviates from that of the corresponding sample in adjacent groups by a number of the sample values smaller than said given number;
    a fifth step of adding together said sample values in each of said groups thereby to produce sums each associated with each of said groups;
    a sixth step of arithmetically determining the difference in said sums for every two adjacent groups and dividing said difference by the sum associated with one of said two adjacent groups thereby to produce quotients; and
    a seventh step of adding together said quotients obtained for every two adjacent groups thereby to produce a total sum, representing the concentration of the item in concern.

2. A method according to claim 1, wherein at said fourth step, said plurality of sample values are grouped into groups each containing a given number of the serial sample values, each of said groups including samples whose positional number deviates from that of the corresponding sample in the adjacent groups by one sample value.

3. A method according to claim 1 or 2, wherein at said first step, two types of light quantities at two different wavelengths are transmitted, and at said second step, the difference between said two types of transmitted light quantities is converted into an electrical transmission signal.

4. A method according to claim 3, wherein said item in concern is an enzyme.

5. A method according to claim 4, wherein said concentration represents the activity of said enzyme.

6. A method according to claim 1, further including an eighth step of displaying said concentration.

7. A method of automatically and optically analyzing a solution comprising:
    a first step of transporting successively a series of solutions to be analyzed, light absorbence of each of the solutions changing with the lapse of time;
    a second step of irradiating a particular solution to be analyzed with light while the particular solution stays at a light irradiating position where the solution is irradiated with the light to thereby obtain a light at at least one specific wavelength transmitted through the solution;
    a third step of converting the quantity of the transmitted light at said at least one specific wavelength into an electrical analog signal during a predetermined period not larger than the period during which the particular solution is irradiated with the light;
    a fourth step of subjecting said analog signal obtained on the basis of the quantity of said transmitted light at said at least one specific wavelength to A-D conversion to thereby obtain a multiplicity of digital transmission signals;
    a fifth step of obtaining a plurality of transmission data by sampling said digital transmission signals at given intervals while said digital transmission signals are produced;
    a sixth step of grouping said plurality of transmission data into groups each containing a predetermined number of said transmission data selected for every given number of said transmission data, each of said groups being deviated from the adjacent groups by a number of the transmission data smaller than said given number;

a seventh step of adding together said transmission data in each of said groups thereby to produce sums each associated with each of said groups;

an eighth step of arithmetically determining the difference between said sums for every two adjacent groups and dividing said difference by the sum associated with one of said two adjacent groups thereby to produce quotients;

a ninth step of adding together said quotients obtained for every two adjacent groups thereby to produce a total sum;

a tenth step of arithmetically determining concentration of the item in concern obtained in said sample on the basis of said total sum; and an eleventh step of displaying said concentration by means of a display unit.

8. A method according to claim 7, wherein at said sixth step, said plurality of transmission data are grouped into groups each containing a given number of the serial transmission data, each of said groups being deviated from the adjacent groups by one transmission data.

9. A method according to claim 7 or 8, wherein said second step obtains a light at two of said specific wavelengths transmitted through the solution, said third step converts each of the quantities of the transmitted light at said two specific wavelengths into an electrical analog signal, and said fourth step subjects the difference between the two analog signals obtained from the quantities of said transmitted light at said two specific wavelengths at each point in time to A-D conversion.

* * * * *